(12) United States Patent
McVay (10) Patent No.: US 7,661,929 B1
(45) Date of Patent: Feb. 16, 2010

(54) CEILING FAN SCENT HOLDER AND PLACEMENT HANDLE

(76) Inventor: Angela Jean McVay, 647 N. Ute Ave., Montrose, CO (US) 81401

( * ) Notice: Subject to any disclaimer, the term of this patent is extended or adjusted under 35 U.S.C. 154(b) by 504 days.

(21) Appl. No.: 11/374,266

(22) Filed: Mar. 13, 2006

Related U.S. Application Data (60) Provisional application No. 60/662,719, filed on Mar. 17, 2005.

(51) Int. Cl.
*F04D 29/38* (2006.01)
(52) U.S. Cl. .................... 416/62; 416/146 R
(58) Field of Classification Search ............ 416/5, 416/62, 146 R; 15/144.3, 144.4; 422/122, 422/123, 124
See application file for complete search history.

(56) References Cited

U.S. PATENT DOCUMENTS 3,550,486 A * 12/1970 Edwards ............... 81/125
5,722,814 A * 3/1998 Yu ..................... 416/204 R 2005/0031498 A1 * 2/2005 Held ..................... 422/124

* cited by examiner

*Primary Examiner*—Edward Look
*Assistant Examiner*—Ryan H Ellis
(74) *Attorney, Agent, or Firm*—Crossley Patent Law; Mark Ashley Crossley (57) ABSTRACT

A ceiling fan scent holder and placement handle which allows a user to distribute fragrance or aromatic substances into the air by using ceiling fans is provided. Said scent holder comprises a lune-shaped piece with an interior channel into which is placed a scent packet, vent holes in each side of a scent holder, and a magnet affixed to the holder top or holder bottom. Said scent holder may be removably placed inside a bracket well of a blade mounting bracket or removably attached to other parts of a ceiling fan via said magnets or also using hook and loop fasteners. A placement handle, comprising a telescopic handle with rotatable arm having at least one magnet affixed between or to prong located at the arm's distal end, may be used to easily place or attach a scent holder in a user-determined ceiling fan location.

3 Claims, 7 Drawing Sheets

CEILING FAN SCENT HOLDER AND PLACEMENT HANDLE

CROSS-REFERENCE TO RELATED APPLICATIONS

Provisional Application 60/662,719
Filing Date Mar. 17, 2005.

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

The present ceiling fan scent holder and placement handle allows a user to distribute fragrance or aromatic substances into the air using ceiling fans. Prior art teaches a multitude of scent or fragrance distribution devices. Prior fragrance distribution devices provide aerosol and pump spray air fresheners, ceramic freshener diffusers, electric potpourri pots, light bulb fragrance rings, oil warmers, incense, and candles. Various problems are associated with each of these devices, however. For instance, light bulb fragrance rings are easily broken and may burn an unwary user's hand since such fragrance rings become hot when used. Candles present safety hazards such as fire when left unattended and burning flesh from the spillage of hot wax. Incense, ceramic freshener diffusers, and oil warmers also present fire as a potential safety hazard. Aerosol and pump spray pair fresheners offer potential health hazards by diffusing liquid particles into the air to be breathed in by a user. In addition aerosol and pump spray air fresheners require a user to actively spray air freshener. Electric potpourri pots often consume precious space on kitchen or bathroom countertops or table space. In addition, many of the prior art freshener devices distribute scent in a limited area. The present ceiling fan scent holder and placement handle addresses problems presented by prior art fragrance distribution devices in that it fits within a common ceiling fan thus not occupying countertop or table space; it does not present fire hazards; it does not diffuse liquid particles into the air to create potential health hazards; and it is not easily broken. The present ceiling fan scent holder and placement handle offers a device by which fragrance may be distributed to a large area, without the hazards presented by prior art devices.

FIELD OF THE INVENTION

This invention is related to fragrance or aromatic distribution devices and method of use.

SUMMARY OF THE INVENTION

The present invention is a ceiling fan scent holder and placement handle. A ceiling fan scent holder comprises a lune-shaped piece with an interior channel into which is placed a scent envelope or other aromatic products which will fit therein. Vent holes in each side of a scent holder allow the scent or fragrance to be distributed. A scent holder is adapted to be placed within a ceiling fan bracket well, secured onto a magnetic screw on a ceiling fan blade, attached to the top side of a ceiling fan blade, attached to a ceiling fan motor, or attached to a ceiling fan base. A scent holder may be formed of heavy plastic, wood or metal. A scent holder may also be placed on other metal surfaces, such as a refrigerator, oven hood, or lamp, or by using hook and loop fasteners or tape, a scent holder may be attached to variety of non-metal surfaces, such as kitchen cabinets, doors, or trash cans. However, the purpose of the invention is not limited to any particular attachment method, placement method, or aromatic distribution method. A scent holder is adapted to encompass a variety of fragrances or aromatic products which accommodate aromatic distribution. A scent holder may be used to contain commercially available aromatic sources or may be used to hold a user-designed aromatic substance. A ceiling fan placement handle comprises a telescopic handle to which is attached a rotatable arm. Said rotatable arm comprises a plurality of prong at its distal end. A magnet or several magnets are placed between or affixed to said prong and may be held into place by securing means, such as duct tape, double-sided tape, or hook and loop fasteners, on the lower and upper sides of said prong.

Certain aspects of the present device overcome one or more drawbacks of the previous art and/or advance the state-of-the-art of fragrance or aromatic distribution devices and, in addition, may meet one or more of the objects as stated hereinbelow. Said device generally comprises a scent holder designed to hold a fragrance packet and a placement handle to place a scent holder in a user-desired location, such as on a ceiling fan. Said scent holder may be placed within a ceiling fan mounting bracket or attached to a ceiling fan blade, a ceiling fan base, or a ceiling fan motor and does not occupy countertop or table top space, which often is a commodity in many homes. The present scent holder does not present fire as a safety hazard or distribute liquid particles into the air which may present health hazards. The present scent holder allows fragrances, aromatics, or scent to be circulated throughout one or more rooms without using any batteries, plugs or outlets. Distribution of such fragrances, aromatics, or scents occurs even when a ceiling fan is stationary. The present scent holder is easy and convenient to use. Thus has been outlined, rather broadly, the more important features of a ceiling fan scent holder and placement handle in order that the detailed description thereof that follows may be better understood and in order that the present contribution to the art may be better appreciated. There are, of course, additional features of the present ceiling fan scent holder and placement handle which will be described hereinafter.

Numerous objects, features and advantages of the invention will be readily apparent to those of ordinary skill in the art upon reading the following detailed description of presently preferred, but nonetheless illustrative, examples of the invention when taken in conjunction with the accompanying drawings. In this respect, before explaining the current examples of the invention in detail, it is to be understood that the invention is not limited in its application to the details of construction and arrangements of the components set forth in the following description or illustration. The invention is capable of other examples and of being practiced and carried out in various ways. It is also to be understood that the phraseology and terminology employed herein are for purposes of description and should not be regarded as limiting.

Those skilled in the art will appreciate that the conception upon which this disclosure is based may readily be utilized as a basis for the design of the structures, methods and systems for carrying out the several purposes of the invention. It is therefore important that the description be regarded as including such equivalent constructions insofar as they do not depart from the spirit and scope of the present invention.

An object of this invention is to provide a ceiling fan scent holder and placement handle which has all of the advantages of the prior art and none of the disadvantages.

An object of the present invention is to provide a scent or fragrance distribution device which uses a ceiling fan typically available in many homes.

Another object of this invention is to avoid fire as a safety hazard while simultaneously distributing fragrance or a scent in to the air in a home or office environment.

It is yet another object to avoid a health hazard presented by fragrance distribution devices distributing liquid particles into the air.

Another object of the present ceiling fan scent holder and placement handle is to provide a simple, easily used, and virtually maintenance-free fragrance distribution device.

Another object of the present ceiling fan scent holder and placement handle is to allow the distribution of fragrances, aromatics or scents throughout one or more rooms without using any batteries, plugs, or outlets.

Distribution of fragrance, aromatics, or scents in a larger area than many of prior art fragrance distribution devices offer is yet another object of the present ceiling fan scent holder and placement handle.

Other objects, features, and advantages of the present invention will become more readily apparent from the following detailed description of the preferred embodiment when considered with the attached drawings.

DRAWINGS—REFERENCE NUMERALS

| 10 | scent holder |
| 15 | holder top |
| 20 | holder side |
| 25 | holder end |
| 30 | holder bottom |
| 35 | channel |
| 37 | vent hole |
| 40 | securing means |
| 45 | magnet |
| 50 | magnet strip |
| 55 | scent packet |
| 60 | fan |
| 62 | fan base |
| 64 | fan motor |
| 65 | fan blade |
| 67 | magnetic screw |

-continued

| 70 | blade top outer end |
| 75 | blade top inner end |
| 80 | blade bracket |
| 82 | bracket well |
| 85 | placement handle |
| 90 | telescopic handle |
| 95 | pivot |
| 100 | arm |
| 105 | prong |
| 110 | adhesive material |
| 115 | magnet |

The scent packet, fan, fan base, fan motor, fan blade, blade top outer end, blade top inner end, blade bracket, bracket well are not part of the claimed invention but are shown for illustrative purposes only.

DETAILED DESCRIPTION OF THE DRAWINGS

With reference now to the drawings and in particular FIGS. 1 through 7 thereof, an example of a ceiling fan scent holder and placement handle employing the principles and concept of the present invention and generally designated by the reference number 10 and 85, respectively, will be described.

Figure 1:
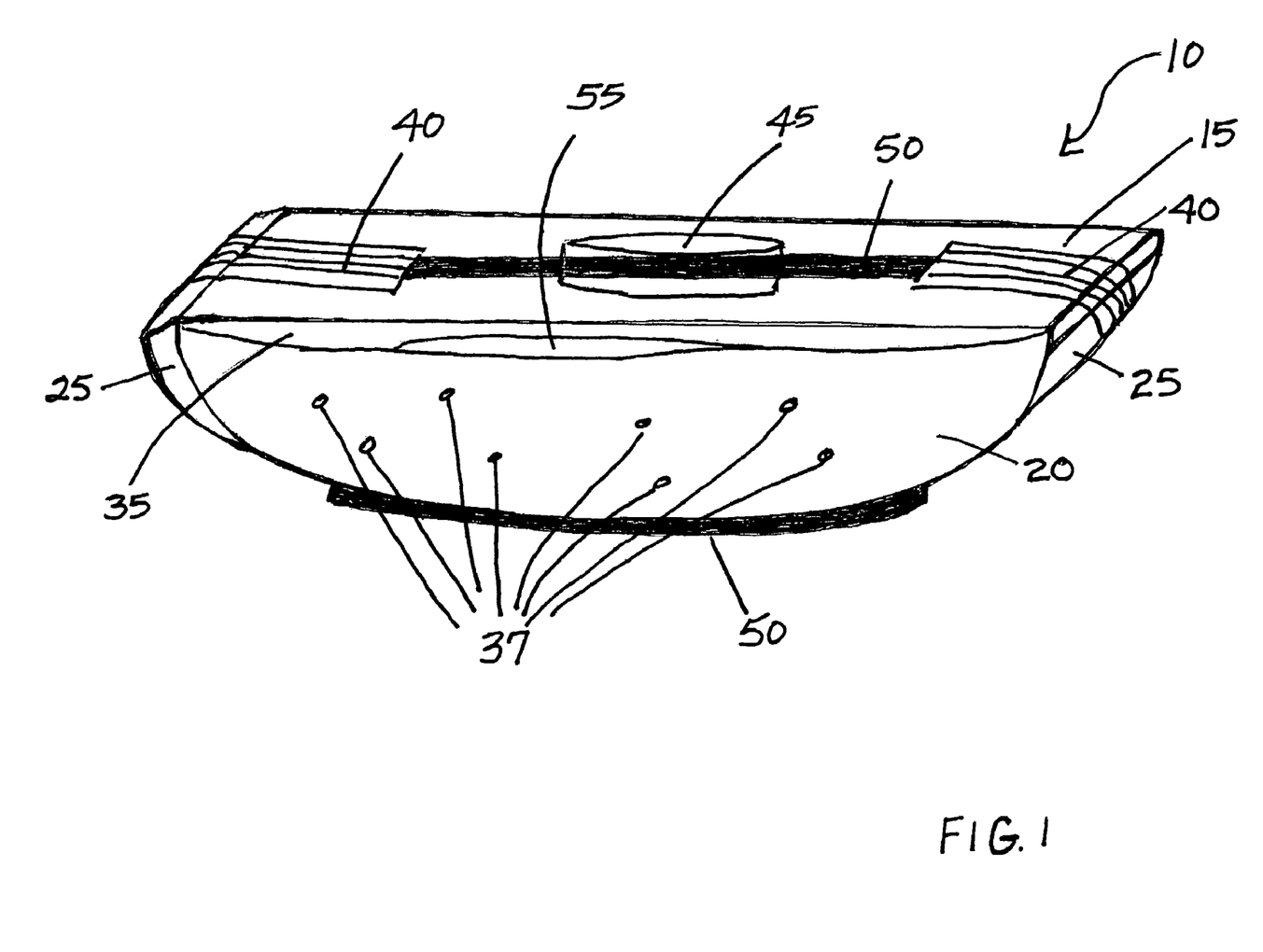
FIG. 1—perspective view of a ceiling fan scent holder.
Figure 2:
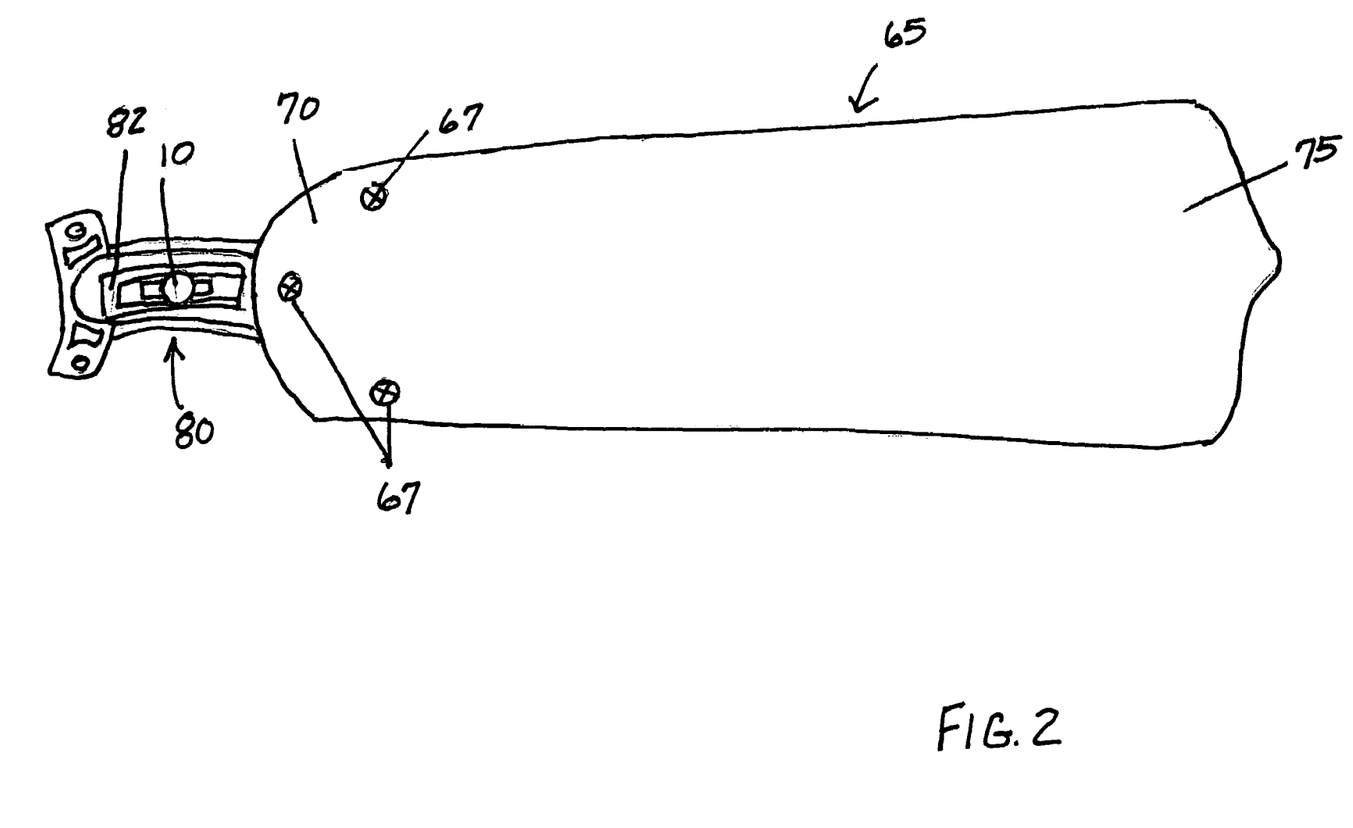
FIG. 2—top plan view of a ceiling fan scent holder inserted within a bracket well of a ceiling fan blade bracket.
Figure 7:
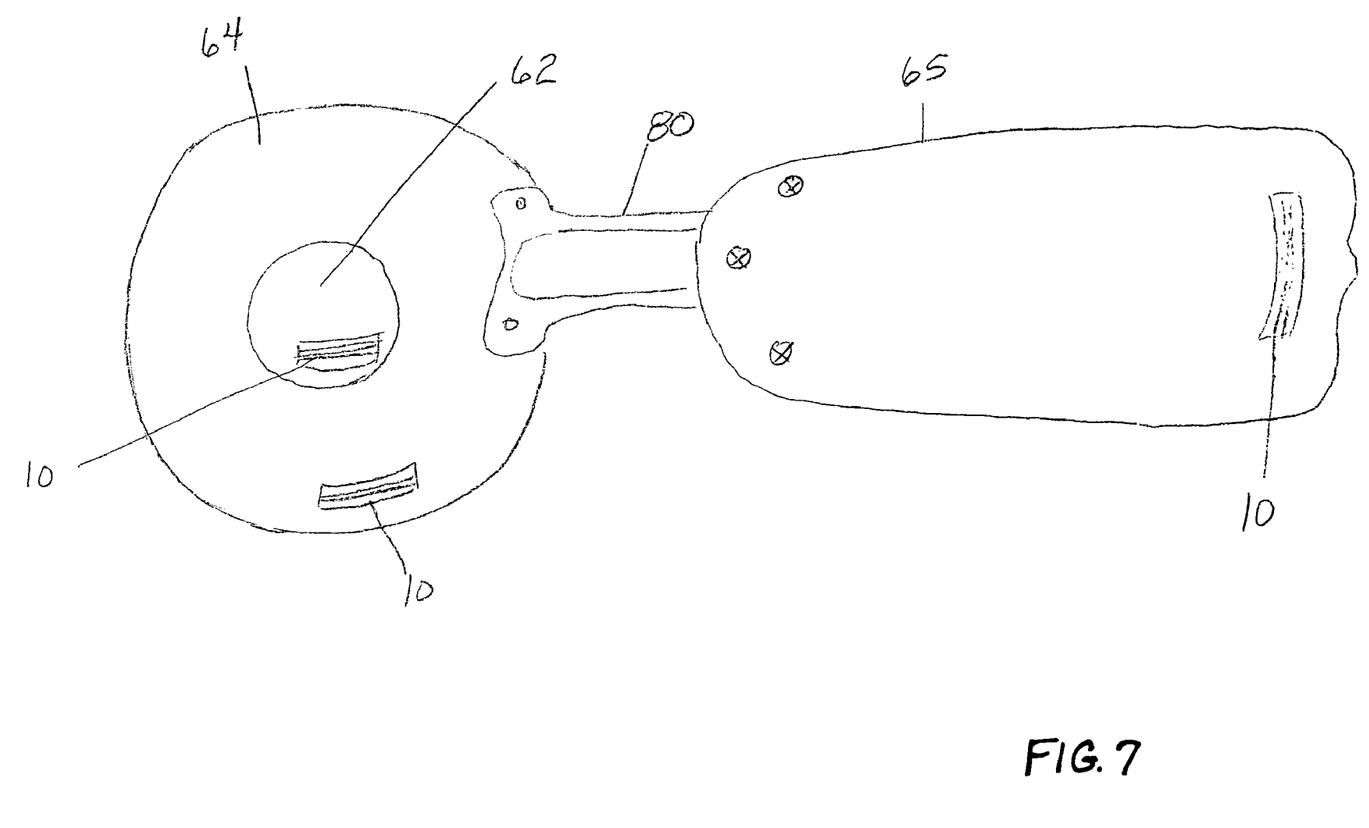
FIG. 7—top plan view of fan blade, fan base, and fan motor illustrating scent holder in various exemplary positions.

FIG. 1 shows perspective view of a ceiling fan scent holder 10. Said scent holder 10 comprises a lune-shaped piece, which may be formed of heavy plastic, wood, metal or other appropriate materials. Said scent holder 10 comprises, a holder top 15, a holder side 20 on each of its two sides, a holder end 25 on each end of its two ends, and a holder bottom 30. Said scent holder 10 with an interior channel 35 running the length of the scent holder 10. A scent packet 55 or other aromatic products, which will fit therein, are placed into said channel 35. A plurality of vent hole 37 are punctured into each holder side 20. Vent holes 37 promote distribution of a scent or fragrance contained in a scent packet 55 into the air within a room or rooms. A scent holder 10 is of a size to be placed within a ceiling fan bracket well 82, shown in FIG. 2. FIG. 1 illustrates a magnet 45 affixed to a holder top 15 by the use of securing means 40, such as tape, double-sided tape, hook and loop fasteners, glue and other adhesive materials, wrapped around said scent holder 10. A magnetic strip 50 may also be affixed to the holder bottom 30 as shown in FIG. 1. In addition to being placed within a channel 35 as shown in FIG. 1, a scent holder 10 may also be secured onto a magnetic screw 67 on a ceiling fan blade 65 (as shown in FIG. 2, attached to the top side of a ceiling fan blade 65 (as shown in FIG. 7), attached to a ceiling fan motor 64 (as shown in FIG. 7), or attached to a ceiling fan base 62 (as shown in FIG. 7). A scent holder 10 may also be placed on other metal surfaces, such as a refrigerator, oven hood, or lamp, or by using hook and loop fasteners or tape, a scent holder may be attached to variety of non-metal surfaces, such as kitchen cabinets, doors, or trash cans. However, the purpose of the present scent holder 10 and placement handle 85 is not limited to any particular attachment method, placement method, or aromatic distribution method. A scent holder 10 is adapted to encompass a variety of fragrances or aromatic products accommodating aromatic distribution. A scent holder 10 may be used to contain commercially available aromatic sources or may be used to hold a user-designed aromatic substance.

FIG. 2 is a top plan view of a ceiling fan scent holder 10 inserted within a bracket well 82 of a ceiling fan blade bracket 80 attached to a blade top inner end 70. FIG. 2 also illustrates a plurality of magnetic screw 67 affixed to a blade top inner end 70. A scent holder 10 may be attached to a fan blade 65 by placing it such that it will affix to a magnetic screw 67.

Figure 3:
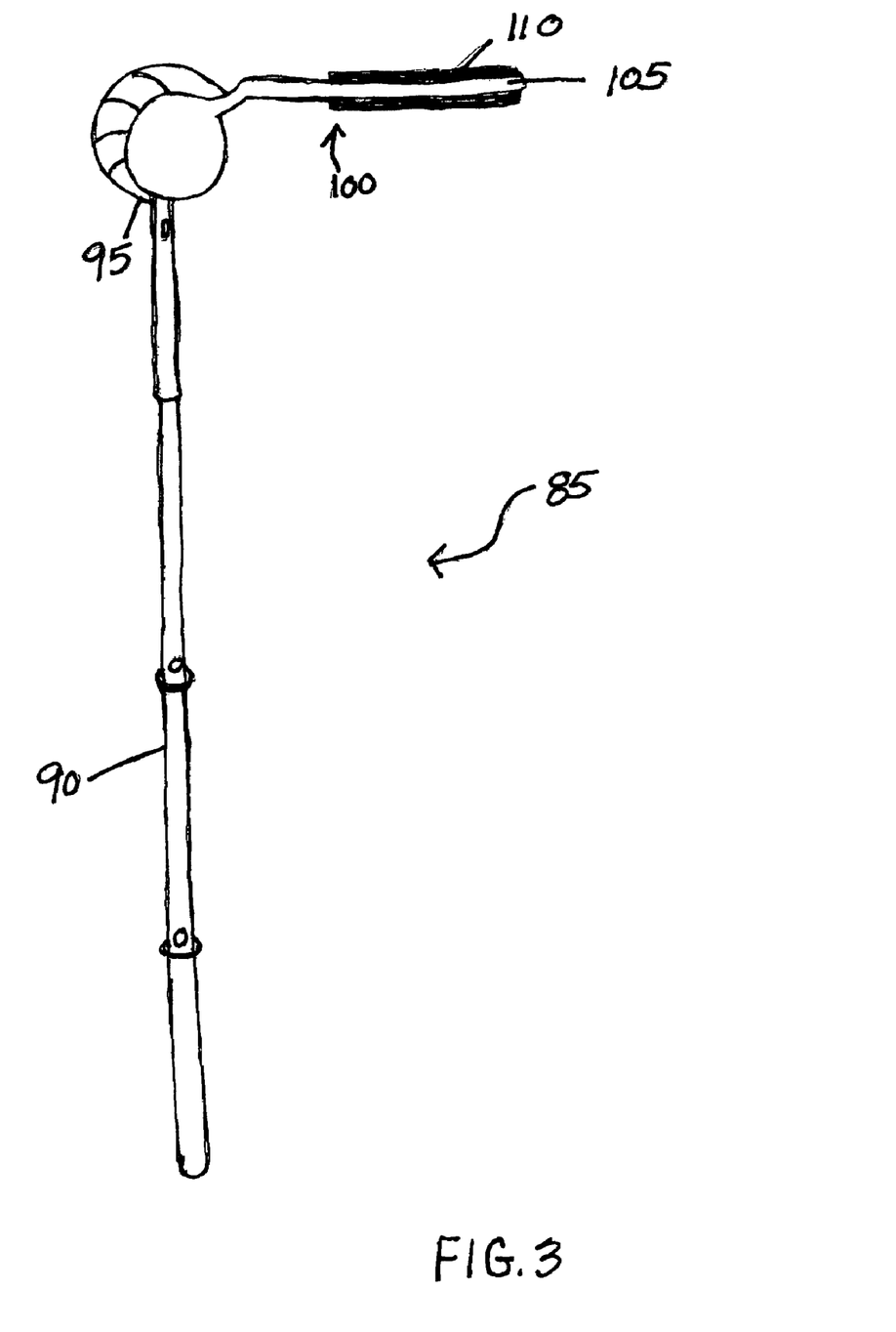
FIG. 3—side elevation view of a placement handle.
Figure 4:
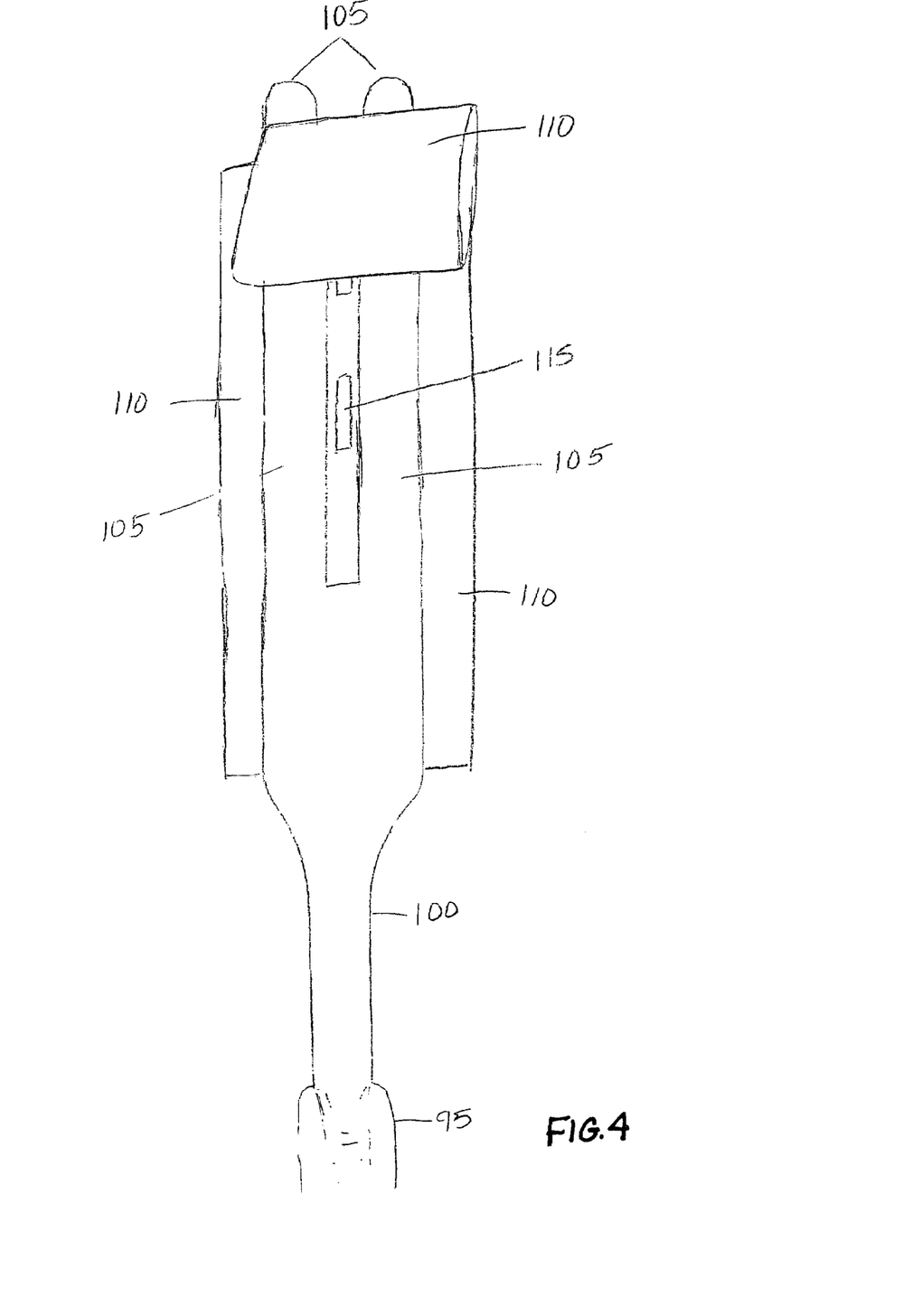
FIG. 4—top plan view of extended arm of a placement handle illustrating magnets positioned between prongs using tape.

FIG. 3 side elevation view of a placement handle 85, which is used to place a scent holder 10 into a ceiling fan bracket well 82 (as shown in FIG. 2) or in another user-desired location on a ceiling fan such as shown in FIG. 7. A placement handle 85 comprises a telescopic handle 90 to which is attached a rotatable arm 100. Said rotatable arm 100 is rotatable due to a pivot 95 (also shown in FIG. 4) located between said telescopic handle 90 and said rotatable arm 100. Said rotatable arm 100 comprises a plurality of prong 105 at its distal end. FIG. 4 illustrates at least one magnet 115 placed between said prong 105 and held into place by adhesive material 110, such as tape, duct tape, double-sided tape, hook and loop fasteners, on the top and bottom surfaces of said prong 105 as shown in FIG. 4.

FIG. 4 is a top plan view of extended arm 100 of a placement handle 85 illustrating magnets 115 positioned between prongs, 105 using adhesive material 110. Adhesive material 110 on the top surface of said prong 105 is illustrated folded back toward the distal end of said prong 105 to reveal the positioning of magnets 115. Magnets 115 may also be affixed directly to said prong 105.

Figure 5:
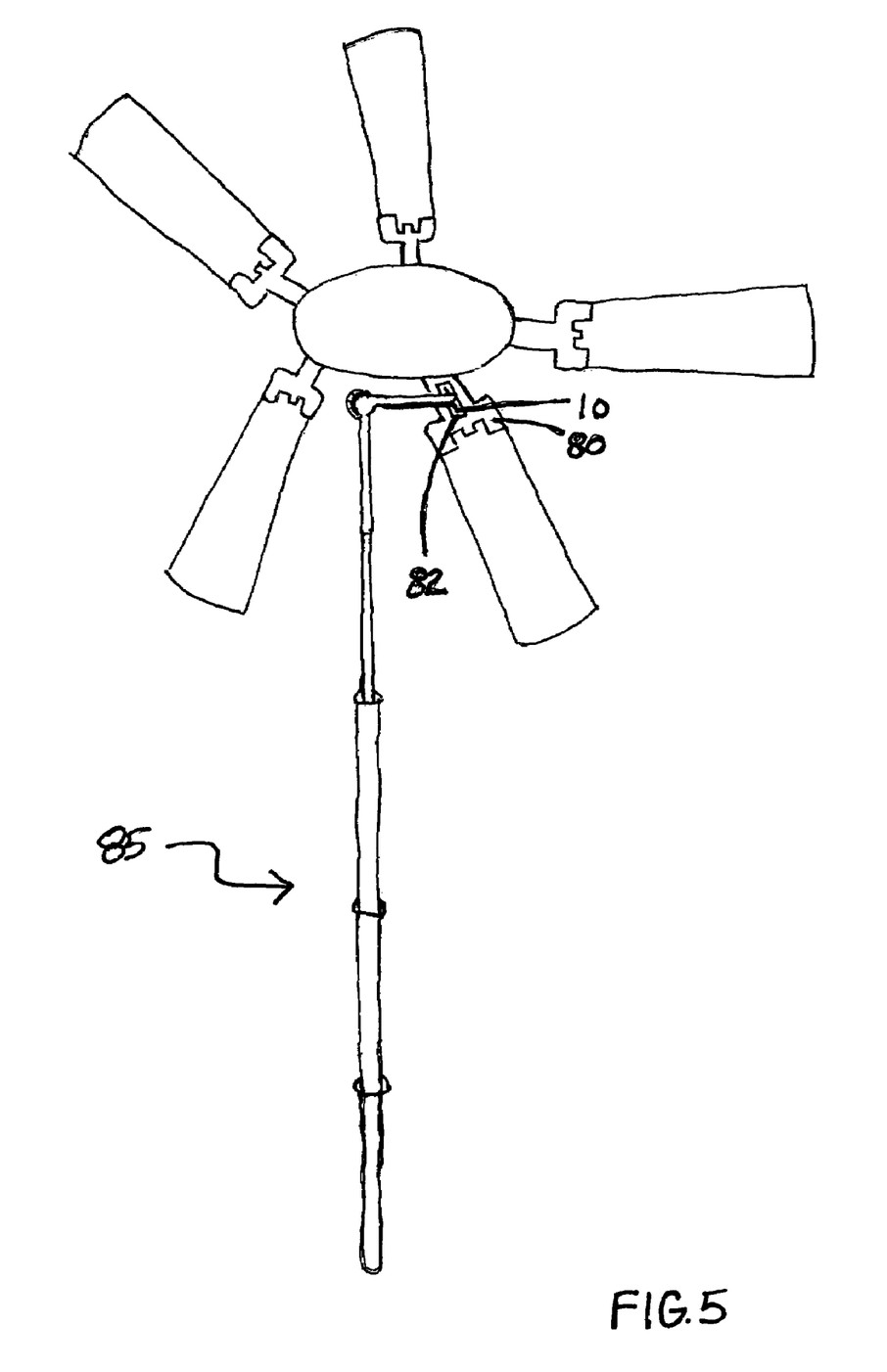
FIG. 5—perspective view of placement handle in use to place a scent holder within a blade bracket as shown in FIG. 2.

FIG. 5 is a perspective view of placement handle 85 in use to place a scent holder 10 within a blade well 82 of a blade bracket 80 as shown in FIG. 2

Figure 6:
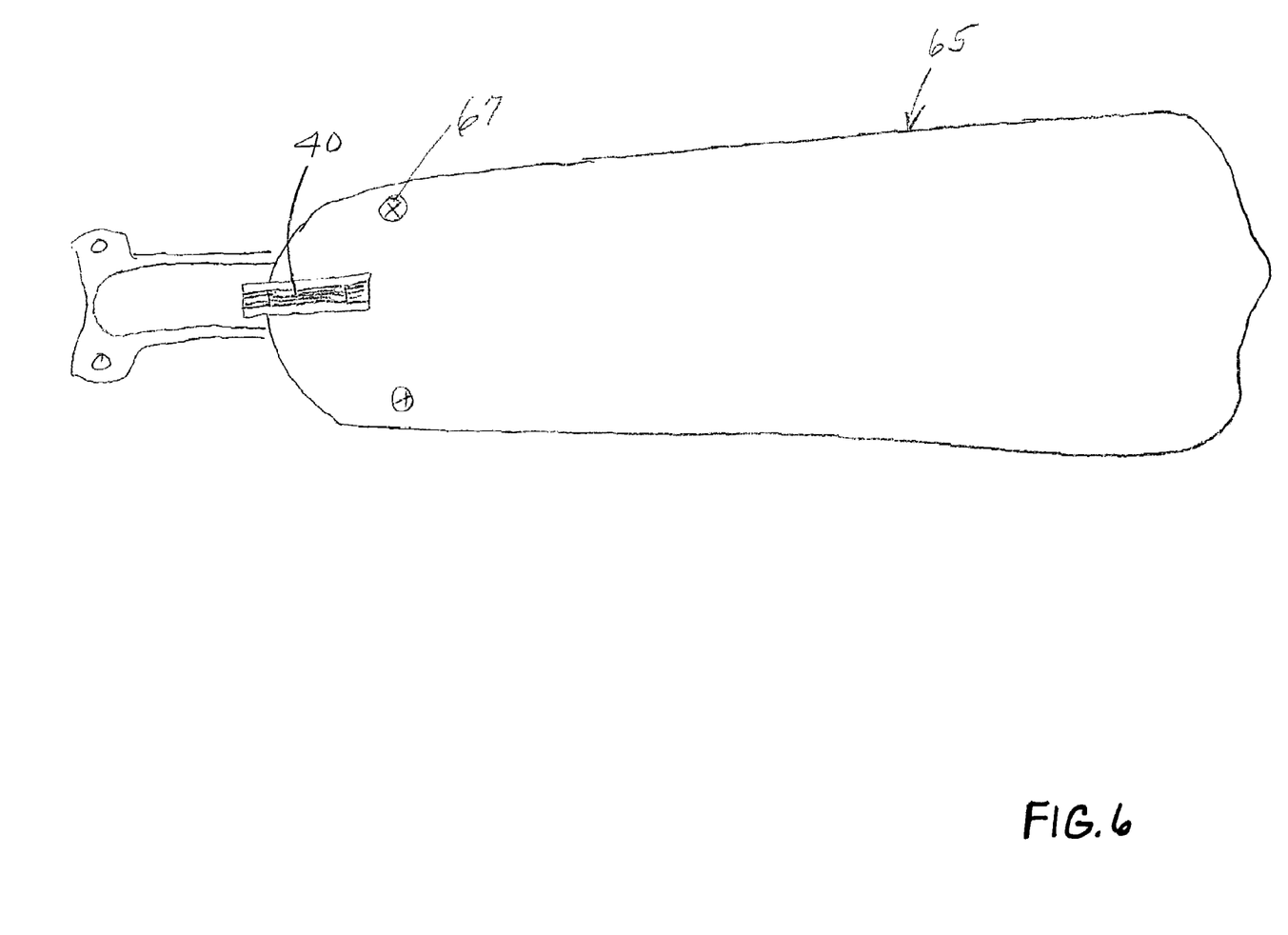
FIG. 6—bottom plan view of scent holder attached to magnetic screw located on fan blade.

FIG. 6 is a bottom plan view of scent holder 10 attached to magnetic screw 67 located on fan blade 65.

FIG. 7 is a top plan view of fan blade 65, fan base 62, and fan motor 64 illustrating scent holder 10 in various exemplary positions.

With respect to the above description then, it is to be realized that the optimum dimensional relationships for the parts of the ceiling fan scent holder and placement handle to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the present invention.

Directional terms such as "front, "back", "in", "out", "downward", "upper", "lower", and the like may have been used in the description. These terms are applicable to the examples shown and described in conjunction with the drawings. These terms are merely used for the purpose of description in connection with the drawings and do not necessarily apply to the position in which the present invention may be used.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

OPERATION

A user selects a scent source or scent packet 55 appropriately sized to fit within a scent holder 10. Said scent source or scent packet 55 should be of a type which will not spill when being circulated, by the, movement of a ceiling fan. Said user places said scent source or scent packet 55 into a channel 35 located within said scent holder 10 as shown in FIG. 1. Said user may removably place said scent holder 10 within a bracket well 82 as shown in FIG. 2 and FIG. 5 or attach said scent holder 10 to various parts of a ceiling fan such as to a magnetic screw as shown in FIG. 6, to a fan blade 65, a fan base 62 or a fan motor 64 as shown in FIG. 7.

A user may more easily place a scent holder 10 within a bracket well 82 or attach said scent holder 10 to other parts of a ceiling fan by using a placement handle 85 as shown in FIG. 3. Said user would removably attach a scent holder 10 to said placement handle 85 so that said scent holder 10 so that the user-determined magnet 45 or magnet strip 50 of said scent holder 10 and the magnet 115 located within the placement handle 85 will attract. Said user may adjust the length of the telescopic handle 90 and lock the length into place and place the arm 100 of the placement handle 85 into a position by rotating said arm 100 as best for appropriately placing said scent holder 10 into a user-determined position. A placement handle may also be used to remove and replace a scent holder 10.

What is claimed is:

1. A ceiling fan scent holder system comprising in combination:
   a lune-shaped piece having a holder top, a holder end on each of two ends, a holder side on each of two sides, and a holder bottom;
   a plurality of spaced-apart vent holes randomly disposed throughout each of the two holder sides of the lune-shaped piece;
   a channel within the interior of said lune-shaped piece running the length of said lune-shaped piece, wherein said channel receives a scent packet;
   a magnet attached to said holder top;
   a telescopic placement handle having a distal end, said handle comprising:
      a pivot member attached to said handle distal end;
      an arm pivotally engaging said pivot member;
      at least one prong disposed on a distal end of said arm;
      at least one magnet disposed on said prong;
   wherein said piece fits into a bracket well of a ceiling fan blade bracket.

2. A ceiling fan scent holder system comprising in combination:
   a lune-shaped piece having a holder top, a holder end on each of two ends, a holder side on each of two sides, and a holder bottom;
   a plurality of spaced-apart vent holes randomly disposed throughout each of the two holder sides of the lune-shaped piece;
   a channel within the interior of said lune-shaped piece running the length of said lune-shaped piece, wherein said channel receives a scent packet
   a magnet strip disposed on said holder bottom;
   a telescopic placement handle having a distal end, said handle comprising:
      a pivot member attached to said handle distal end;
      an arm pivotally engaging said pivot member;
      at least one prong disposed on a distal end of said arm;
      at least one magnet disposed on said prong;
   wherein said piece fits into a bracket well of a ceiling fan blade bracket.

3. A ceiling fan scent holder system comprising in combination:
   a lune-shaped piece having a holder top, a holder end on each of two ends, a holder side on each of two sides, and a holder bottom;
   a plurality of spaced-apart vent holes randomly disposed throughout each of the two holder sides of the lune-shaped piece;

a channel within the interior of said lune-shaped piece running the length of said lune-shaped piece, wherein said channel receives a scent packet a magnet attached said holder top and a magnet strip attached to said holder bottom;

a telescopic placement handle having a distal end, said handle comprising:

a pivot member attached to said handle distal end;

an arm pivotally engaging said pivot member;

at least one prong disposed on a distal end of said arm;

at least one magnet disposed on said prong;

wherein said piece fits into a bracket well of a ceiling fan blade bracket.

* * * * *